(12) United States Patent
Ghinelli

(10) Patent No.: US 7,871,646 B2
(45) Date of Patent: Jan. 18, 2011

(54) USE OF A HUMAN AMNIOTIC MEMBRANE COMPOSITION FOR PROPHYLAXIS AND TREATMENT OF DISEASES AND CONDITIONS OF THE EYE AND SKIN

(75) Inventor: Emiliano Ghinelli, Boston, MA (US)

(73) Assignee: Repsco LLP, London (GB)

( * ) Notice: Subject to any disclaimer, the term of this patent is extended or adjusted under 35 U.S.C. 154(b) by 0 days.

(21) Appl. No.: 11/977,659

(22) Filed: Oct. 25, 2007

(65) Prior Publication Data

US 2008/0108045 A1 May 8, 2008

Related U.S. Application Data

(62) Division of application No. 10/665,188, filed on Sep. 17, 2003, now abandoned.

(60) Provisional application No. 60/411,738, filed on Sep. 18, 2002.

(51) Int. Cl.
*A61K 35/12* (2006.01)
*A61K 35/50* (2006.01)
(52) U.S. Cl. .................. 424/520; 424/582; 424/583
(58) Field of Classification Search .......... 424/520, 424/582, 583
See application file for complete search history.

(56) References Cited

U.S. PATENT DOCUMENTS

| 5,002,071 | A | 3/1991 | Harrell |
| 5,932,205 | A | 8/1999 | Wang et al. |
| 6,117,857 | A | 9/2000 | Carlsson et al. |
| 6,143,315 | A | 11/2000 | Wang et al. |
| 6,326,019 | B1 | 12/2001 | Tseng |

FOREIGN PATENT DOCUMENTS

| GB | 2110531 | 6/1983 |
| KR | 2001 100 588 | 11/2001 |
| KR | 2001 098716 A | 11/2001 |
| KR | 2001 100588 | 11/2001 |

OTHER PUBLICATIONS

Na et al. 1999. Analysis of Human Amniotic Membrane Components as Proteinase Inhibitors for Development of Therapeutic Agent for Recalcitrant Keratitis. Trophoblast Research 13:453-466.*
Snowman. 1988. Lyophilization: Freeze-Drying A Downstream Process. Downstream Processes: Equipment and Techniques, Alan R. Liss, Inc. p. 1-2.*
Ti et al. 2002. Factors Affecting Outcome Following Transplantation of Ex vivo Expanded Limbal Epithelium on Amniotic Membrane for Total Limbal Deficiency in Rabbits. Investigative Ophthalmology & Visual Science, Aug. 2002, vol. 43, No. 8. p. 2584-2592.*
Stedman's Medical Dictionary 27th Edition. 2009. Definition for the term 'extract'. p. 1.*
Orlacchio, A., et al.; "beta-N-Acetyl-d-glucosaminidase isoenzymes from human amnionic membranes"; Clinica Chimica ACTA, Elsevier BV Amsterdam, NL; (1986); 159(3): 279-289.
Database WPI Week 200230; Thomson Scientific, London, GB; AN 2002-251929; XP002528367 & KR 2001 098 716 (Bioland Ltd.) (2001) (abstract).
Database WPI Week 199713; Thomson Scientific, London, GB; AN 1997-143797; XP002528368 & RU 2 063 761 C1 (Pilipenko Yu G) (1996) (abstract).

* cited by examiner

*Primary Examiner*—Taeyoon Kim
(74) *Attorney, Agent, or Firm*—Weingarten, Schurgin, Gagnebin & Lebovici LLP

(57) ABSTRACT

A method of preparing an amniotic membrane extract including the steps of obtaining a healthy amniotic membrane from a pregnant mammal, such as a pig, cow, horse or human, homogenizing the membrane to obtain a homogenate solution, freezing the homogenate solution, and lyophilizing the frozen homogenate solution to dryness is disclosed. Preferably, the lyophilized homogenate is pulverized to a powder. The lyophilized homogenate is then reconstituted before use, e.g., in a liquid, such as a balanced salt solution or fresh amniotic fluid, or in another substance, such a gel, an ointment, a cream or a soap, depending on the intended use. Also disclosed is a pharmaceutical composition prepared according to the method of the invention, for prophylaxis and/or treatment of a disease or condition, especially of the eye or the skin. Exemplary pharmaceutically acceptable carriers for the composition of the invention include an ophthalmic solution for eye drops, a gel, an ointment, an emulsion, a cream, a powder and a spray.

10 Claims, 4 Drawing Sheets

DAY 0

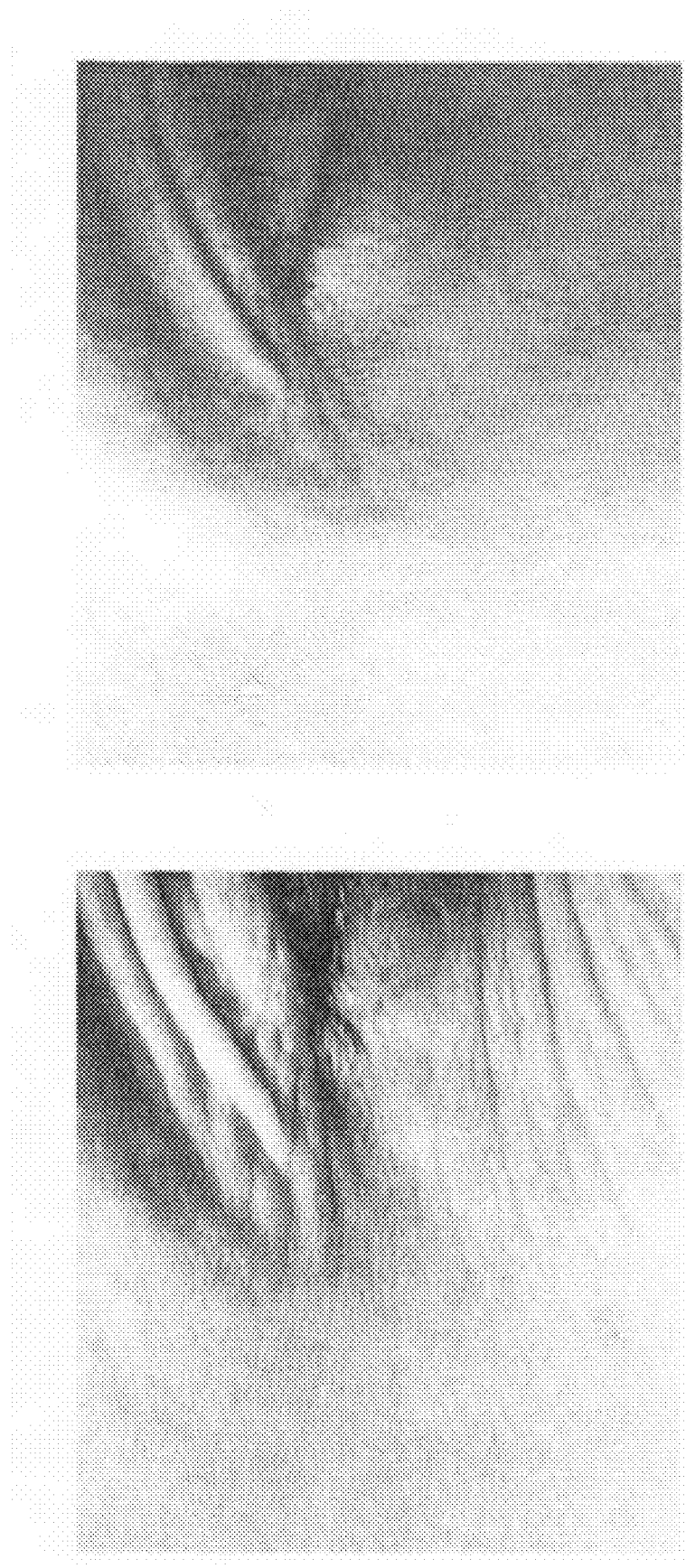
FIG. 4A  DAY 0
FIG. 4B  DAY 14

USE OF A HUMAN AMNIOTIC MEMBRANE COMPOSITION FOR PROPHYLAXIS AND TREATMENT OF DISEASES AND CONDITIONS OF THE EYE AND SKIN

CROSS REFERENCE TO RELATED APPLICATIONS

The present application is a divisional application of U.S. application Ser. No. 10/665,188, filed Sep. 17, 2003 now abandoned and entitled USE OF A HUMAN AMNIOTIC MEMBRANE COMPOSITION FOR PROPHYLAXIS AND TREATMENT OF DISEASES AND CONDITIONS OF THE EYE AND SKIN, which claims the priority of U.S. Provisional Application No. 60/411,738 filed Sep. 18, 2002 entitled, EXTRACT OF HUMAN AMNIOTIC MEMBRANE FOR TREATMENT OF OCULAR INJURIES AND DISEASES, the whole of which are hereby incorporated by reference herein.

STATEMENT REGARDING FEDERALLY SPONSORED RESEARCH OR DEVELOPMENT

N/A

BACKGROUND OF THE INVENTION

Corneal epithelium integrity and corneal sensory innervation play a pivotal role in maintaining ocular surface health (Tseng et al., 1997). Clinical conditions leading to corneal nerve disruption associated with epithelial defects and persistent and progressive corneal ulcers include viral infections, autoimmune and endocrine diseases, thermal and chemical burns, multiple ocular surgeries and V pair ganglion or sensory routes affections (Donzis et al., 1987; Gould, 1967; Hyndiuk et al., 1977; and Liesegang, 1985). Current therapeutic strategies adopted for such conditions include medical therapy (e.g., tear substitutes, topical and systemic drugs), surgical approaches based on amniotic membrane transplantation (Chen et al., 2000), and, quite recently, a panacea of novel compounds, especially growth factors able to promote effectively corneal epithelial re-growth. These molecules, mainly neuropeptides, include epidermal growth factor (Kandarakis et al., 1984), aldose reductase inhibitors (Hosolani et al., 1995), insulin-like growth factor type I associated with Substance P, and nerve growth factor (Lambiase et al., 1998). In particular, amniotic membrane tissue has shown powerful and interesting properties in bringing about the anatomical recovery of the anterior ocular surface from a disease condition, along with observations regarding its composition that include even more growth factors than the list mentioned above (Uchida et al., 2000). Unfortunately, an improvement in the patient's visual outcome following application of amniotic membrane tissue is often unsuccessful (Solomon et al., 2002). Application of the amniotic membrane as a multilayer structure instead of as a monolayer has been somewhat more effective, which may be due to the quantity of amniotic membrane applied biological factors (Prabhasawat, 2001). Cryopreserved human amniotic membrane has been applied to the affected eye of a patient as a patch after defrosting (Kim et al., 1995). The applied patch released a restricted amount of factors to the damaged tissue, but the survival of the human amniotic membrane cells decreased to zero in a few days.

Despite the partial effectiveness of these approaches, these treatments are usually unable to completely restore the affected part, functionally and anatomically. Accordingly, a more effective and efficient approach in treating the symptoms and clinical conditions of ocular diseases and related conditions would be useful.

BRIEF SUMMARY OF THE INVENTION

These objectives are achieved using the compositions and methods according to the invention. In one aspect, the invention is directed to a method of preparing an amniotic membrane extract in which the method includes the steps of obtaining a healthy amniotic membrane from a pregnant mammal, such as a pig, cow, horse or human, homogenizing the membrane to obtain a homogenate solution, freezing the homogenate solution, and lyophilizing the frozen homogenate solution to dryness. Preferably, the lyophilized homogenate is pulverized to a powder. The lyophilized homogenate is then reconstituted before use, e.g., in a liquid, such as a balanced salt solution or fresh amniotic fluid, or in another substance, such a gel, an ointment, a cream or a soap, depending on the intended use.

In another aspect, the invention is directed to a pharmaceutical composition for prophylaxis and/or treatment of a disease or condition, the composition including a therapeutically effective amount of an amniotic membrane extract prepared according to the method of the invention and dispersed in a pharmaceutically acceptable carrier for administration to a patient. Exemplary pharmaceutically acceptable carriers include an ophthalmic solution for eye drops, a gel, an ointment, an emulsion, a cream, a powder and a spray. Furthermore, the amniotic membrane extract may be distributed on a bandage or a medicinal contact lens for local administration to a patient.

In a further aspect, the invention is directed to a method of prophylaxis and/or treatment of a disease or condition, the method including the steps of providing a patient in need of such prophylaxis and/or treatment, and administering an effective amount of the pharmaceutical composition of the invention to the patient. Exemplary diseases or conditions treatable by the method of the invention include persistent corneal ulcer, Ocular Cicatritial Pemphigoid, Stevens-Johnson syndrome, conjunctival inflammation, dry eye, Sjöngren's syndrome, chemical or thermal injuries, multi-surgery effects, contact lenses over-wear, severe microbial infections, neurotrophic keratitis, ischemic keratitis, peripheral ulcerative or inflammatory keratitis, limbitis aniridia, pterigium or pseudopterigium, and multiple endocrine deficiency. For ocular use, the pharmaceutically acceptable carrier preferably includes preservative free eye drops.

In yet another aspect, the invention is directed to a kit that includes a therapeutically effective amount of an amniotic membrane extract prepared according to the method of the invention and instructions for the use thereof. Preferably, the kit further includes a pharmaceutically acceptable carrier for administering the amniotic membrane extract to a patient. The amniotic membrane extract according to the invention has the healing properties of amniotic membrane tissue, but at an enhanced level, and can be used according to the invention without the need for costly surgical procedures.

BRIEF DESCRIPTION OF THE FIGURES

Other features and advantages of the invention will be apparent from the following description of the preferred embodiments thereof and from the claims, taken in conjunction with the accompanying figures, in which:

FIGS. 4A and 4B depict photographs of a patient having enhanced wrinkling adjacent to the eye at day 0 (FIG. 4A) and day 14 (FIG. 4B) after treatment with the composition of the invention (1.5× magnitude).

DETAILED DESCRIPTION OF THE INVENTION

Figure 1A:
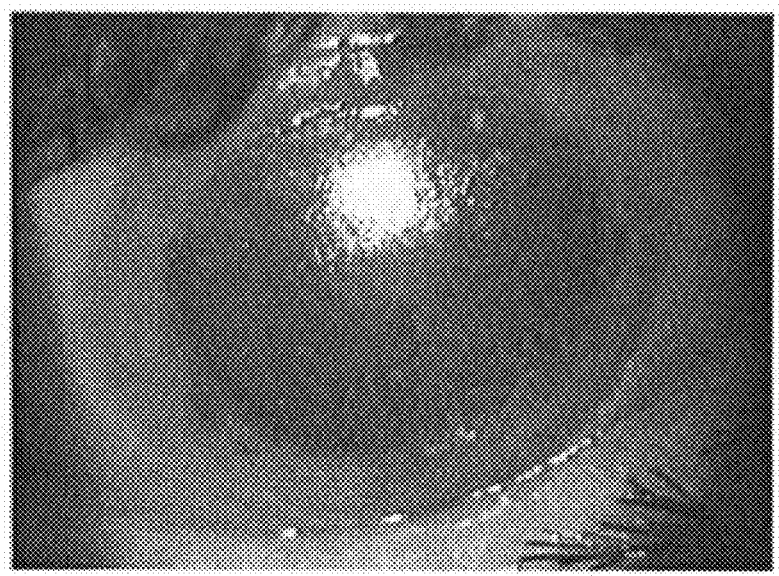
FIGS. 1A (white light) and 1B (UV light) are photographs showing the eye of a patient with Ocular Cicatritial Pemphigoid at day 0 (2.5× magnitude)

The therapeutic composition of the invention comprises a healthy amniotic membrane extract derived from the amniotic membrane of a pregnant mammal, e.g., a human, a pig, a cow, or a horse. A healthy amniotic membrane is one that has been maintained under sterile conditions and that has been determined to be virus free, e.g., free from the hepatitis-B and C viruses and human immunodeficiency virus, and free from bacterial contamination. The amniotic membrane is, preferably, freshly obtained and quickly processed for preparation of the extract according to the invention, as described herein. The membrane may be stored prior to preparation of the extract. However, storage of the amniotic membrane tissue will result in some loss in cell viability.

The amniotic membrane extract according to the invention has the healing properties of amniotic membrane tissue, but at an enhanced level, and can be used according to the invention without the need for costly surgical procedures. The application of the therapeutic composition of the invention may be performed by a physician or by a capable patient at home. The composition is straightforward to prepare and may be constituted to contain any concentration of factors desired, depending on the severity of the disease or condition to be treated. The treatment may be administered as necessary without incurring undesirable side effects.

The composition of the invention is useful for treating ocular diseases and/or skin disorders and many other diseases when used in accordance with the method of the invention, as described herein. Ocular Cicatritial Pemphigliod (OCP), for example, is known to be a rare immunological related disease that involves the anterior ocular surface leading to blindness despite any kind of therapeutic approach (Foster, 1986). Therapeutic choices like anti-inflammatory drugs, steroids and immunosuppressive agents help to control the disease but very often are unable to block its natural progression. The natural history of OCP begins with recurrent conjunctival inflammations and then fibrosis, associated with fornix foreshortening, symblepharon and entropion, progressively leading to a dry eye syndrome and culminating with keratinization of the ocular surface, along with corneal limbal stem cell deficiency associated with corneal ulcer formation, all as a result of the prolonged status of inflammation (Tsai et al., 1995 and Foster et al., 1982).

A recent clinical report describes the effects of amniotic membrane transplantation in the mid-late stage (II-IV) of OCP patients. This surgical approach is considered a strategy to restore the anterior ocular surface anatomy, to maintain the fornix depth, and to reduce conjunctival inflammation (Barabino et al., 2003). Even if OCP patients may benefit from the use of multi-layer amniotic membrane transplantation, the beneficial effect of this therapy is frequently transient, and low final visual acuity is often observed. It has not yet been explained if the increasing effectiveness of multi-layer amniotic membrane transplantation is related to an increase in the mechanical support to the affected tissue or due to the higher amount of factors released by the multi-layered amniotic membranes. It is also not understood why multiple applications of amniotic membranes still are not able to completely manage the disease. A plausible explanation may be related to the biphasic course of OCP, i.e., an immediate conjunctival immune reaction, plus the changes due to this inflammation, that, when they begin, are rendered irreversible by a cascade of effects. Early diagnosis and treatment is then crucial.

In an experiment described herein, use of the composition of the invention blocked OCP progression in a human patient. The OCP was monolateral and at a relatively early stage. Treatment according to the method of the invention did not include surgery and resulted in a stable outcome. These findings suggest that treatment with amniotic membrane extract in accordance with the invention is highly effective in OCP early stage.

In addition, based on the present findings, treatment with the composition according to the invention should be considered in many anterior ocular surface conditions (see infra), whether they have immunological involvement or not, in which amniotic membrane transplantation currently shows limited effects, including lids and conjunctival inflammation associated with deep corneal ulcers.

Accordingly, in one aspect, the invention is directed to a novel extract of amniotic membrane for treating, e.g., visual system and other organ injuries or diseases. Exemplary visual system injuries or diseases that the therapeutic composition of the invention may be used to treat are as follows: for the reconstruction of the ocular surface in patients with limbal stem cells deficiency (Tseng et al., 1998); for the treatment of visual system age-related diseases in general; for reconstruction of the ocular surface in patient with corneal persistent epithelial defect (Tseng et al., 1998); for corneal epithelial healing and to avoid corneal stromal remodeling and haze formation after photorefractive keratectomy (Woo et al., 2001); as a substance that can promote and support healing processes following ocular surface damage related to Stevens Johnson Syndrome and OCP (Tsubota et al., 1996); for healing support and a therapeutic approach in other eye anterior surface diseases including dry eye, Sjögren's syndrome, thermal and chemical burns, and acute and chronic inflammation; and as a versatile compound that can treat the causes of total and partial epithelial stem cells deficiency. Exemplary total epithelial stem cell deficiencies include, but are not limited to, chemical and thermal injuries, Stevens Johnson Syndrome, multi-surgery effects in the limbal region, contact lens overwear and severe microbial infections. Exemplary partial epithelial stem cell deficiency include, but are not limited to, neurotrophic keratitis, ischemic keratitis, peripheral ulcerative and inflammatory keratitis, limbitis, aniridia, pterigium, pseudopterigium and multiple endocrine deficiency (Tseng et al., 1998; Uchida et al., 2000).

Other exemplary uses of the composition according to the invention are as a treatment for skin dystrophies, burn injury and skin ulcers (Trelford et al., 1979); as a therapy for chemiotheraphic stomatitis; as an immunomodulator in autoimmune disease; to increase tolerance in the treatment of auto-, allo- and xeno-transplants; as an osteoinductive property substance for guided bone regeneration (Gomes et al., 2001); as a substance that can be incorporated in the actual hardware currently used for bacterial and other simple organism culture in vitro or in vivo; as a substance that can be incorporated in currently used devices dedicated to cell culture, such as cell culture dishes, a three-dimensional matrix or a gel (Uchida et al., 2000); as a storage or culture medium for human cells; as a part of an integrated delivery system that will transport the effective compound from an accessible site to the site in need, for remote release of all the beneficial effects of the amniotic membrane; as a bone and tissue anti-inflammatory drug; as a source of factors and receptors for used in neuro-degenerative or inflammatory diseases; and as a source of receptors that mediate glucose transport.

The amniotic membrane extract according to the invention comprises all of the cytokines in a fresh amniotic membrane, e.g., growth factors, receptors and molecules necessary for, e.g., wound healing and other effects. The term "cytokines" includes, but is not limited to, growth factors, interleukins, interferons and colony stimulating factors. Growth factors include, but are not limited to, epidermal growth factor, fibroblast growth factor, nerve growth factor, mast cell-stimulating growth factor and Schwann cell growth factor. These factors are present in normal tissue at different stages of tissue development, marked by cell division, morphogenesis and differentiation. Among these factors are stimulatory molecules that provide the signals needed for in vivo tissue repair. These cytokines can stimulate repair of injured tissue.

In one aspect, the amniotic membrane extract of the invention can be in the form of a powder, where the homogenated amniotic membranes have been lyophilized to dryness. Samples of a frozen homogenate can be processed in a lyophilizer to remove all the water content from the homogenate and to form a powder. The lyophilized powder should be stored at least under refrigeration (4° C.) and preferably at −20° C. The powder can be transported where needed and reconstituted gently (e.g., preferably without shaking or stirring, at 4° C.), protected from light and under sterile conditions at neutral pH, e.g., in balanced salt solution (or other carriers such as gels, ointments, creams, soaps, suspensions, membranes, 3D matrix, delivery systems, biological carriers, etc.) before use. At least four hours should be allowed for the powder to dissolve or be dispersed in the delivery medium. The extract according to the invention also can be reconstituted, or diluted, if desired, with fresh amniotic fluid, autologous serum from a prospective patient or other liquid medium.

In yet another aspect of the invention, the therapeutic composition can be used as an ingredient in cosmetics, to improve wound healing, for example, for patients affected by facial dermabrasion and other skin dystrophies (Kucan, 1982). Other exemplary cosmetic uses may include, but are not limited to, moisturizing and treating dry and sensitive skin, providing anti-aging effects and improving the health of hair roots. The amniotic membrane composition according to the invention may also be used, e.g., as an anti-wrinkle, anti-aging moisturizer; in eczematoid skin conditions; in psoriasis vulgaris skin conditions; in acne vulgaris skin condition; in unspecified or idosyncratic inflammatory skin conditions; and as a compound to hydrate and moisturize pressure ulcers, diabetic ulcers, ischemic ulcers, and any other kind of dystrophic ulcers.

The therapeutic compositions of the invention may be administered topically or by routine methods in pharmaceutically acceptable inert carrier substances. For example, the compositions of the invention may be administered in a sustained release formulation using a biodegradable biocompatible polymer, or by on-site delivery using micelles, gels, ointments or liposomes. For example, for skin disorders or for cosmetic purposes, the amniotic membrane composition of the invention may be administered in a spreadable ointment. The human amniotic membrane extract of the invention can be administered in different dosages as described below (e.g., several times per day at an amount from 1 □g to 1 mg amniotic membrane tissue equivalents per administration), as appropriate. Optimal dosage and modes of administration can readily be determined by conventional protocols.

The therapeutic compositions of the invention can be administered independently or co-administered with another agent as desirable. For example, an extract of another vital organ such as the placenta could also be included. It is contemplated that the therapeutic compositions of the invention will be particularly useful for ocular diseases and conditions, for example, when administered in preservative-free eye drops containing an antibacterial agent.

The therapeutic compositions of the invention can also be prepared as a kit for the curative or prophylactic treatment of disease with instructions for use thereof. The kit of the invention may comprise the amniotic membrane extract in powder form or provided in a saline solution in a pharmaceutically acceptable carrier vehicle, or incorporated in different carriers, media or matrices.

The contents of all references, pending patent applications and published patent applications, cited throughout this application are hereby incorporated by reference.

The following examples are presented to illustrate the advantages of the present invention and to assist one of ordinary skill in making and using the same. These examples are not intended in any way otherwise to limit the scope of the disclosure.

Example I

Preparation of the Amniotic Membrane Extract

In an exemplary isolation procedure, the amniotic membrane was removed from a pregnant woman in the operating room, at the moment of Caesarian parturition, dissected from the other tissues of the placenta and rinsed in a sterile solution, e.g., phosphate-buffered saline (PBS) as described by Kim et al., 1995. Sections of the amniotic membrane were divided into one cm square pieces under sterile conditions and stored at 4° C. in PBS containing 1000 U/ml penicillin and 20 mg/ml streptomycin until processing.

The following procedures were all carried out at 4° C. and neutral pH (approximately 7.4) under sterile conditions and with protection from direct light: Amniotic membrane pieces were weighed and the volume was adjusted to reach a ratio of the g of amniotic membrane/ml of neutral buffer solution of approximately 0.3. The membrane pieces were then sonicated using a Branson 250 sonicator with 3 steps of 3 min each at the following conditions: 20% duty cycle, output in micro tip limit 8. After a pH check, the homogenate was centrifuged for 10 minutes at 4° C. and 4000 rpm and then the supernatant centrifuged for another 5 minutes at 14000 rpm to get rid of any undesired residues present in the extract.

After another pH check, an aliquot of the homogenate (supernatant) was analyzed by a protein assay to quantify the total protein amount present in the homogenate. The homogenated sample was then filtered through 0.8 micron filters under a sterile hood, protecting the compound from light and overheating 1 and maintaining the homogenate temperature at 4° C. or below. Aliquots of the sample suspension were quickly frozen in 100% ethanol-dry ice and stored at −80° C. until the lyophilization procedure. The aliquots were then lyophilized for 24 hours at −20° C. in a sterile lyophilizer.

According to the above protocol, the approximate amount of homogenated amniotic membrane tissue per 1 ml of solution before lyophilization was about 300-350 mg. Thus, 1 ml aliquots of homogenate, lyophilized, are equivalent to approximately 300-350 mg of amniotic membrane tissue. (This amount of protein was also confirmed by protein assay after reconstitution.) The lyophilized powder was stored (e.g., at −20° C.) for six months at least so as to allow for the growth of any viruses that might have been present but undetected in the original homogenate preparation. Any reconstituted samples testing positive for the presence of viruses will be destroyed.

Lyophilized homogenate was then reconstituted gently at 4° C. and neutral pH, under sterile conditions and protected from light, in an appropriate vehicle and at an appropriate concentration for the intended use. For the high concentrations used at the start of the treatment protocol of Example II, the lyophilized homogenate was reconstituted at approximately 8 mg amniotic tissue equivalents/ml balanced salt solution (BSS). Before use, a sample of the reconstituted stock was re-tested for the presence of any viruses.

Example II

Treatment of an Ocular Condition in a Human Patient

A patient who developed Ocular Cicatritial Pemphigoid (OCP) and who had refused many available treatments was successfully treated with the novel composition of the invention. The treatment was for a short period of time, but this treatment was able to stabilize the patient's clinical condition even after use of the amniotic membrane composition was discontinued.

Figure 1B:
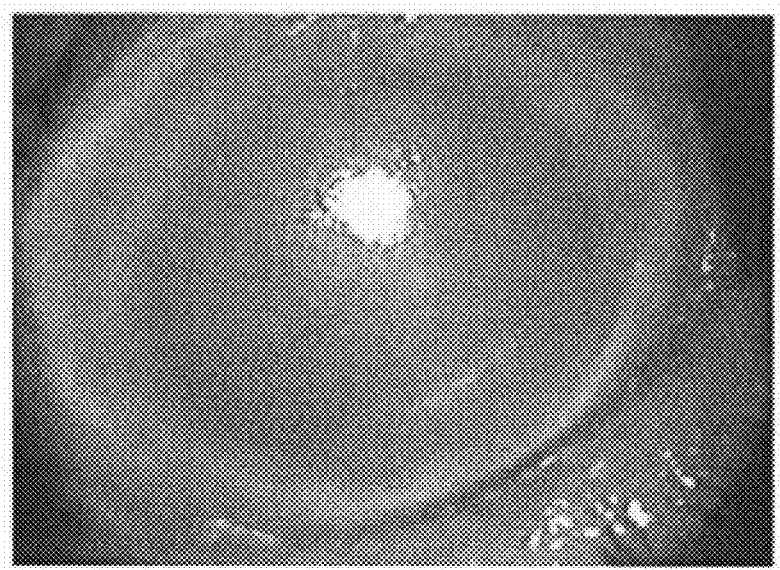

In July 2001, a 57 year old female patient was identified with a history of asymmetric intense burning-like pain, foreign body sensation, photophobia, epiphora and mucous discharge with a severely low visual acuity in the right eye (able to see hand movements). She had an absence of corneal sensitivity (established looking for a change in Cochet-Bonnet esthesiometer reading), a chronic corneal ulcer extended to the limbus (FIGS. 1A and 1B, day 0) and inferior fornix foreshortening with trichiasis but not entropion. She had had previous episodes of conjunctival inflammation followed by inferior lids conjunctiva progressive scars and was diagnosed clinically and histologically as having OCP (showing linear deposition of IgG in the basement membrane). According to the Foster et al. (1982) OCP classification, the patient was compatible with late stage 2 to early stage 3. Her treatment history had included tear substitutes, soft contact lenses and anti-inflammatory drugs. She refused any topical corticosteroids or immunosuppressive agents in combination with short-term steroids or minor surgical procedures. The therapies previously mentioned, including midriatic agents, were able to provide relief for only a short period of time. The conjunctival inflammation did not resolve, and the persistent corneal epithelial defect became chronic. Low visual acuity (e.g., the ability to count a clinician's fingers) was also observed.

The patient's case was managed with the amniotic membrane composition according to the invention in association with other preservative-free eye drops. During the first week of treatment, the treatment protocol included the composition of the invention in high doses (1-2 drops in the affected eye of a composition consisting of 8 mg amniotic membrane tissue equivalents/ml BSS) 5 times a day and with a preservative-free antibiotic (e.g., netilmicina sulfate) 3 times a day, preservative-free artificial tears (e.g., Carbossilmetil-cellulose) 8 times a day and preservative-free Carbomer gel at bedtime. The preservative-free drops were used to prevent bacterial growth and to promote the growth of healing cells. The second and third week of treatment consisted of the composition of the invention at a medium dose (1-2 drops in the affected eye of a composition consisting of 4 mg amniotic membrane tissue equivalents/ml BSS) 3 times a day, preservative-free netilmicina sulfate 2 times a day, preservative-free artificial tears (Carbossilmetil-cellulose) 8 times a day and preservative-free Carbomer gel at bedtime. In the fourth and fifth weeks, treatment consisted of the composition of the invention 3 times a day at a low dose (1-2 drops in the affected eye of a composition consisting of 0.4 mg amniotic membrane tissue equivalents/ml BSS) preservative-free netilmicina sulfate 2 times a day, preservative-free artificial tears (Carbossilmetil-cellulose) 8 times a day and preservative-free Carbomer gel at bedtime. Starting in the sixth week, the use of the amniotic membrane composition was suspended, keeping preservative-free artificial tears (Carbossilmetil-cellulose) treatment every hour in association with soft contact lenses.

Figure 2A:
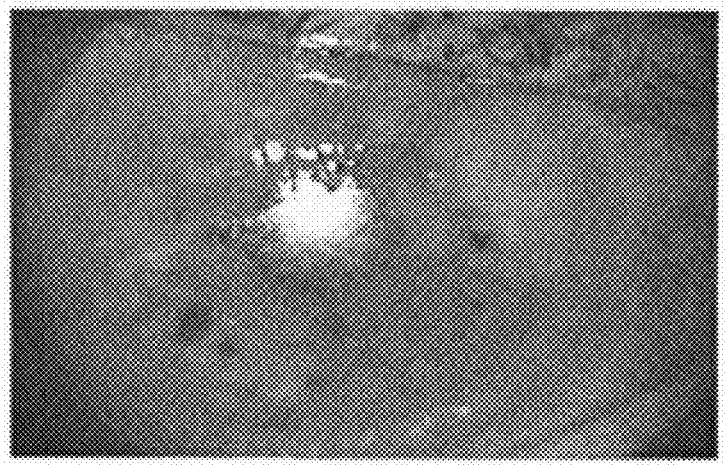
FIGS. 2A (white light) and 2B (UV light) are photographs showing the eye of the patient of FIGS. 1A and 1B at day 10 after treatment with the composition of the invention (2.5× magnitude)
Figure 2B:
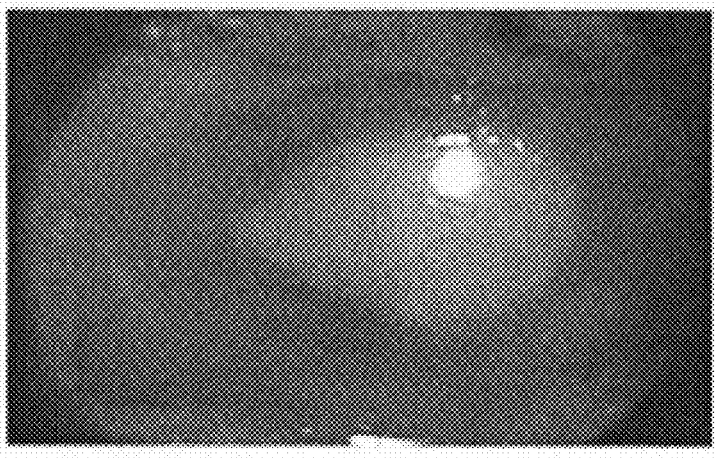
Figure 3A:
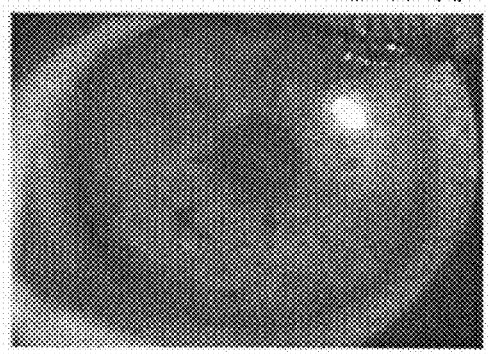
FIGS. 3A (white light), 3B (UV light) and FIG. 3C (white light) are photographs showing the eye of the patient of FIGS. 1A and 1B at day 30 (FIGS. 3A and 3B) and day 40 (FIG. 3C) after further treatment with the composition of the invention (2.5× magnitude)
Figure 3B:
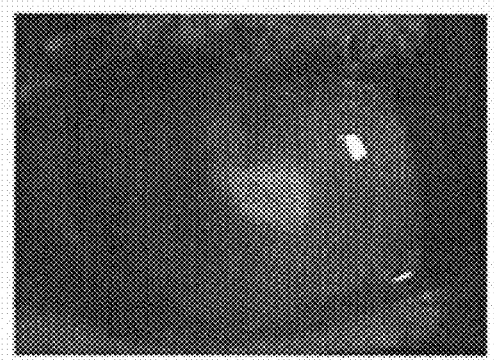
Figure 3C:
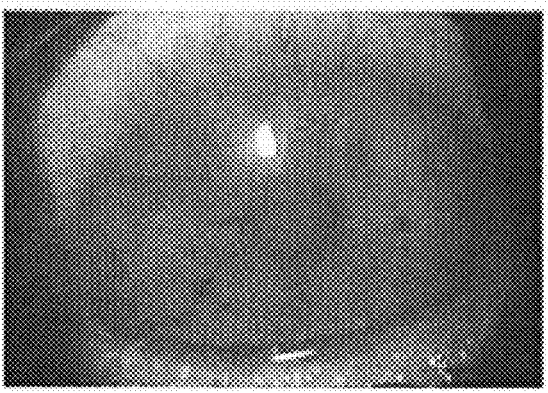

From the very beginning of this therapeutic regimen, the patient began to feel less pain. After a transient limbal and conjunctival inflammation, the pain disappeared totally within 2 weeks along with the burning-like pain, the photophobia and, less rapidly, the conjunctival inflammation previously described. The chronic corneal ulcer resolved completely (FIGS. 2A and 2B, day 10 and FIGS. 3A-3C, days 30 and 40, respectively) within 6 weeks. The patient also recovered her corneal sensitivity and visual acuity (20/200). She had no further episodes of conjunctival inflammation or other episodes of inferior fornix foreshortening and trichiasis. These clinical findings still represent the stable condition of the patient.

Example III

Treatment of a Skin Condition in a Human Patient

A patient having age-related enhanced wrinkling adjacent to the eye was successfully treated with a composition according to the invention. FIG. 4A shows the wrinkling adjacent to the right eye of the patient at day 0. A 0.35 mg/ml amniotic membrane tissue equivalent preparation in a BSS suspension was administered to the patient's skin in the treatment area at a dosage and frequency of 1-2 drops per day, at bed time. After 14 days, the wrinkling was substantially diminished, as shown in FIG. 4B.

The composition according to the invention has also been tested in a cell culture system at a concentration range of 0.3-30 mg/ml and shown to be highly effective in ensuring the function and survival of the cultured cells. Testing of the inventive composition has also been carried out in a corneal injury (scraping) mouse model with recovery substantially to normal within 14 days in corneal transparancy, specularity and reflection.

REFERENCES

Barabino S et al. Role of amniotic membrane transplantation for conjunctival reconstruction in ocular-cicatricial pemphigoid. Ophthalmol. 2003, 474-480.

Chen H J et al. RTF Pires, S C G Tseng. Amniotic membrane transplantation for severe neurotrophic corneal ulcers. Br. J. Ophthalmol. 2000, 84:826-833.

Chikama T et al. Treatment of neurotrophic keratopathy with substance —P— derived peptide (FGLM) and insulin growth factor-1. Lancet 1998, 351:1783-1784.

Donzis P B et al. Management of noninfectious corneal ulcers. Surv. Ophthalmol. 1987, 32:94-110.

Foster C S et al. Immuno-suppresive therapy for progressive ocular cicatricial pemphigoid. Ophthalmol. 1982, 89:340-353.

Foster, C S. Cicatricial pemphigoid. Trans. Am. Ophthalmol. Soc. 1986, 527-663.

Foster, C S et al. Immunosuppressive therapy for progressive ocular cicatricial pemphigoid. Ophthalmol. 1982, 340-353.

Gomes M F et al. Int. J. Oral Maxillofac. Implants 2001, 16(4): 563-71.

Gould H L. Treatment of neurotrophic keratitis with scleral contact lenses. Eye, Ear, Nose and Throat Monthly 1967, 46:1406-14.

Hosolani H et al. Reversal of abnormal corneal epithelial cell morphologic characteristics and reduced corneal sensitivity in diabetic patients by aldose reductase inhibitor, CT-112. Am. J. Ophthalmol. 1995, 119:288-294.

Hyndiuk R A et al. Neurotrophic corneal ulcers in diabetes mellitus. Arch. Ophthalmol. 1977, 95:2193-6.

Kandarakis A S et al. The effect of epidermal growth factor on epithelial healing after penetrating keratoplasty in human eyes. Am. J. Ophthalmol. 1984, 98:411-415.

Kim J C et al. Transplantation of preserved human amniotic membrane for surface reconstruction in severely damaged rabbit corneas. Cornea. 1995, 14:473-484.

Koizumi et al. Curr. Eye Res. 2000, 20:173-7.

Kubo et al. I.O.V.S. 2001, 42:1539-46.

Kuncan J O et al. Amniotic membranes as dressings following facial dermabrasion. Ann. Plast. Surg. 1982, 8:523-7.

Lambiase A et al. Topical treatment with nerve growth factor for corneal neurotrophic ulcers. N. Engl. J. Med. 1998, 338:1174-80.

Sao-Bing Lee et al. Curr. Eye Res. 2000, 20:325-34.

Liesegang T J. Corneal complications from herpes zoster ophthalmicus. Ophthalmol. 1985, 92:316-24.

Prabhasawat P. Single and multilayer amniotic membrane transplantation for persistent corneal epithelial defect with and without stromal thinning and perforation. Br. J. Ophthalmol. 2001, 85:1455-1463.

Saiko U et al. Neurotrophic Function of Conditioned Medium From Human Amniotic Epithelial Cells. J. Neurosci. Res. 2000, 62:585-592.

Solomon A et al. Amniotic Membrane Grafts for non traumatic Corneal Perforations, Descemetoceles, and Deep Ulcers. Ophthalmol. 2002, 109:694-703.

Trelford J D et al. Am. J. Obstet. Gynecol. 1979, 134:833-845.

Tsai R J F et al. Effect of stromal inflammation on the outcome of limbal transplantation for corneal surface reconstruction. Cornea. 1995, 439-449.

Tseng S C G et al. Important concepts for treating ocular surface and tear disorders. Am. J. Ophthalmol. 1997, 124: 825-35.

Tseng et al. Arch. Ophthalmol. 1998, 116:431-441.

Tsubota et al. Am. J. Ophthalmol. 1996, 122:38-52.

Uchida et al. J. of Neurosci. Res. 2000, 62:585-590.

Woo et al. Br. J. Ophthalmol. 2001, 85:345-349.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method of preparing an amniotic membrane extract, said method comprising carrying out the following steps in the order given:

dividing a healthy amniotic membrane from a pregnant mammal into pieces under sterile conditions;

placing said pieces of amniotic membrane in a sterile solution at a known weight to volume ratio;

homogenizing said membrane in said sterile solution by sonication to obtain a homogenate solution;

centrifuging said homogenate solution to obtain a homogenate supernatant;

freezing said homogenate supernatant in aliquots; and lyophilizing said aliquots of frozen homogenate supernatant to dryness to obtain lyophilized homogenate supernatant.

2. The method of claim 1, further comprising the step of processing said lyophilized homogenate supernatant to a powder.

3. The method of claim 1, further comprising the step of reconstituting said lyophilized homogenate supernatant.

4. The method of claim 3, wherein said lyophilized homogenate supernatant is reconstituted in a liquid.

5. The method of claim 4, wherein said liquid is selected from the group consisting of balanced salt solution and fresh amniotic fluid.

6. The method of claim 3, wherein said lyophilized homogenate supernatant is reconstituted in a gel, an ointment, a cream or a soap.

7. The method of claim 1, wherein said amniotic membrane is a human amniotic membrane.

8. The method of claim 1, wherein said amniotic membrane is obtained from a mammal selected from the group consisting of pig, cow and horse.

9. The method of claim 1, wherein said amniotic membrane is freshly obtained.

10. The method of claim 3, wherein said lyophilized homogenate supernatant is reconstituted in quantifiable amounts in a pharmaceutically acceptable carrier.

* * * * *